(12) United States Patent
LaVay et al.

(10) Patent No.: US 7,452,382 B1
(45) Date of Patent: Nov. 18, 2008

(54) POLYMERIC SILICONE POLYSORBATE SOFTENERS

(75) Inventors: Carter LaVay, Riverside, CT (US); Anthony J. O'Lenick, Jr., Dacula, GA (US)

(73) Assignee: Zenitech LLC, Riverside, CT (US)

( * ) Notice: Subject to any disclaimer, the term of this patent is extended or adjusted under 35 U.S.C. 154(b) by 0 days.

(21) Appl. No.: 11/980,660

(22) Filed: Oct. 31, 2007

(51) Int. Cl.
*C11D 3/00* (2006.01)

(52) U.S. Cl. .................. 8/115.51; 424/70.7; 424/70.12; 525/446; 556/437; 556/441

(58) Field of Classification Search ................. 8/115.1; 424/70.7, 70.12; 525/446; 556/437, 441
See application file for complete search history.

(56) References Cited

U.S. PATENT DOCUMENTS

| | | | | |
|---|---|---|---|---|
| 4,724,248 A | * | 2/1988 | Dexter et al. | 524/262 |
| 5,136,063 A | * | 8/1992 | O'Lenick, Jr. | 554/77 |
| 5,210,133 A | * | 5/1993 | O'Lenick, Jr. | 525/54.1 |
| 5,411,729 A | * | 5/1995 | O'Lenick, Jr. | 424/70.12 |
| 5,475,125 A | * | 12/1995 | O'Lenick, Jr. | 556/437 |
| 6,239,290 B1 | | 5/2001 | Buffa | |
| 6,972,123 B1 | * | 12/2005 | O'Lenick, Jr. | 424/78.02 |
| 7,344,708 B1 | * | 3/2008 | LaVay et al. | 424/70.12 |

* cited by examiner

*Primary Examiner*—Lorna M Douyon
*Assistant Examiner*—Bijan Ahvazi

(57) ABSTRACT

The present invention is directed to a class of polyesters that are lightly crosslinked polyesters made by reacting polysorbate units (linked by the reaction of their hydroxyl groups) to the carboxyl group of dimer acid. As will become clear, lightly crosslinked as used herein relates to reactions in which there is an excess of hydroxyl groups on a molar basis to carboxylic groups on the dimer acid. The polymers and a contribute softness, lubricity and antistatic properties when applied to hair, skin, textile fiber and paper.

20 Claims, No Drawings

POLYMERIC SILICONE POLYSORBATE SOFTENERS

RELATED APPLICATIONS

None

FEDERAL SPONSORSHIP

None

FIELD OF THE INVENTION

The present invention is directed to a class of polyesters that are lightly crosslinked polyesters made by reacting polysorbate units, terminal di-hydroxyl silicone compounds (linked by the reaction of their hydroxyl groups) to the carboxyl group of dimer acid. As will become clear, lightly crosslinked as used herein relates to reactions in which there is an excess of hydroxyl groups on a molar basis to carboxylic groups on the dimer acid. The polymers and a contribute softness, lubricity and antistatic properties when applied to hair, skin, textile fiber and paper. The presence of the specific dimer fatty group, and water-soluble polysorbate group provides unique and heretofore unobtainable properties on a variety of substrates. The presence of the linear silicone not only confers improved silicone solubility, but also lowers the viscosity of the resulting product when compared to the same polymer lacking the silicone.

BACKGROUND OF THE INVENTION

Surfactants are a well known materials that possess an oil soluble and a water soluble group. The literature is full of surface active agents that have a fatty hydrophobe and a water soluble hydrophilic portion. Polysorbates arte one class.

Wikiopedia defines polysorbate as an oily liquid. It is a class of emulsifiers used in some pharmaceuticals and food preparation. It is often used in cosmetics to solubilise essential oils into water based products. Polysorbates are derived from PEG-ylated sorbitan (a derivative of sorbitol) esterified with fatty acids. Surfactants that are esters of plain (non-PEG-ylated) sorbitan with fatty acids are usually referred to by the name Span.

U.S. Pat. No. 4,297,290 to Stockberger issued Oct. 27, 1981 teaches that sorbitan fatty acid esters can be prepared by forming anhydro sorbitol (a mixture of sorbitans, isosorbide, and unreacted sorbitol) by acid-catalyzed anhydrization, then reacting the resulting anhydro sorbitol with a fatty acid in the presence of a base at a temperature not exceeding about 215° C. Use of temperatures not over 215° C. results in products having substantially less color than those obtained at higher temperatures.

Polysorbates are emulsifiers, but are sticky on the hair and skin and do not provide appreciable softness, conditioning or antistatic properties.

U.S. Pat. No. 6,800,275 issued to O'Lenick, issued Oct. 5, 2007, incorporated herein by reference discloses "a series of polyester compounds made from the reaction of (a) a difunctional hydroxy compound, specifically polyoxyalkylene glycols, (b) a difunctional carboxylic acid, specifically dimer acid and hydrogenated dimer acid, and (c) a capping carboxylic acid, which only contains one acid group." The patent teaches, "another critical component is the mono-functional carboxylic group, which caps the polymer and provides terminal oil soluble portion to the molecule. This lowers the critical micelle concentration and provides improved skin deposition".

We have surprisingly found that contrary to the teachings of U.S. Pat. No. 6,800,275, the use of a polysorbate, linear not ethoxylated silicone and dimer acid without the required capping fatty acid offers improved lubricity and skin feel.

THE INVENTION

Objective of the Invention

It is the object of the invention to provide materials, which provide outstanding softness, antistatic properties and conditioning properties to a variety of substrates including hair, skin, textile fiber and paper.

Another object of this invention is to provide a process for treating hair, skin and textile fiber with the polyesters of the present invention.

SUMMARY OF THE INVENTION

The present invention is directed to unique polyester made by reaction of dimer acid with polysorbate and linear di-hydroxyl silicone.

Polyesters of this type are complicated mixtures of oligomers. We anticipate that the various hydroxyl groups on the polysorbate offer little regiospecificity, that is react about equally as well as each other. Since the analytical techniques do not yet exist to differentiate the reaction on one or another hydroxyl groups, product by process claims are the optimum way to claim the present reaction product. The product has the repeating groups (either polysorbate or silicone) linked through an ester linkage with dimer acid.

These polyesters because of their structure are outstanding lubricants and skin feel modifiers. While not wanting to be bound by any one theory of operation, we believe that the polyester's lowest free energy from aqueous solution is one in which the fatty group on the polysorbate is orientated toward the substrate, the water soluble polysorbate polyoxyalkylene groups are orientated away from the substrate. This repeating pattern results in a "sewing together" of groups that are captured on the surface of the substrate. The result is a molecule that is "entangled" in the substrate, having the water soluble groups pointing out of the substrate. This results in enhanced durability and hydrophilic surface treatments. A self wetting, conditioner, providing durable softness results. These properties are highly prized in personal care applications including shampoos, body wash, and baby products. The improved hydrophilic properties makes substrates so treated water loving, a requirement for absorbent applications, and a rarity in products that have a lot of fatty content in the molecule.

DETAILED DESCRIPTION OF THE INVENTION

One aspect of the present invention is directed toward a polyester of the present invention made by the reaction of:

(a) a di-hydroxyl silicone conforming to the following structure;

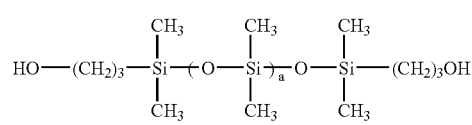

a is an integer ranging from 10 to 100;

and (b) a polysorbate conforming to the following structure

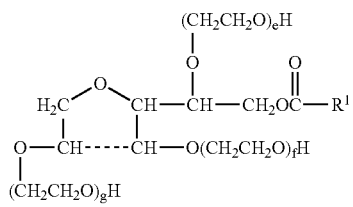

e is an integer, ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;

with dimer acid conforming to the following structure:

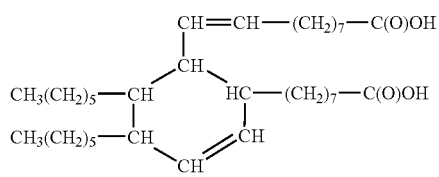

or hydrogenated dimer acid conforming to the following structure:

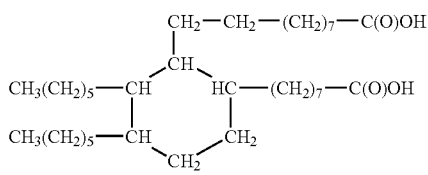

or mixtures thereof;
at a temperature of between 150 and 200° C., said the mole ratio of said carboxyl groups in the dimer acid to hydroxyl group in the polysorbate range from 1:2 to 1:3. This partial crosslinking provides increased molecular weight and improved skin lubricity.

Another aspect of the present invention is directed toward a process for conditioning hair, skin and paper which comprises contacting the hair skin or paper with an effective conditioning concentration of a polyester made by the reaction of:

(a) a polysorbate conforming to the following structure

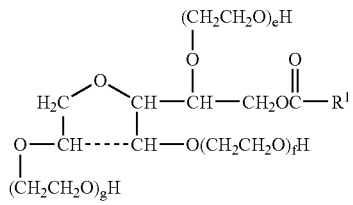

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;
and (b) a di-hydroxyl silicone conforming to the following structure;

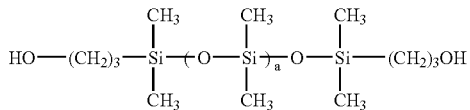

a is an integer ranging from 10 to 100;

with dimer acid conforming to the following structure:

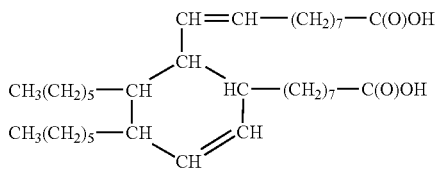

or hydrogenated dimer acid conforming to the following structure:

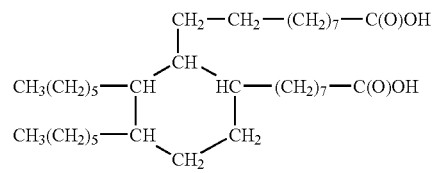

or mixtures thereof;
at a temperature of between 150 and 200° C., said the mole ratio of said carboxyl groups in the dimer acid to hydroxyl group in the polysorbate range from 1:2 to 1:3.

In a preferred embodiment the process is carried out using an effective conditioning concentration ranges from 0.1 to 15% by weight.

PREFERRED EMBODIMENTS

The presence of polyoxyethylene groups $—CH_2CH_2—O)_x$ H on the polysorbate and affects water solubility. In a preferred embodiment where the products are water-soluble the percent polyoxyethylene groups in the molecule ranges from between 40 and 65 percent of the total molecular weight of the polymer.

In a preferred embodiment the dimer acid is hydrogenated dimer acid conforming to the following structure:

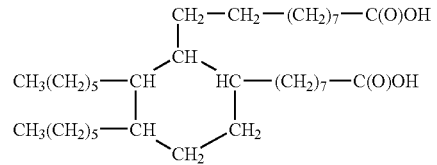

In another preferred embodiment the dimer acid is dimer acid conforming to the following structure:

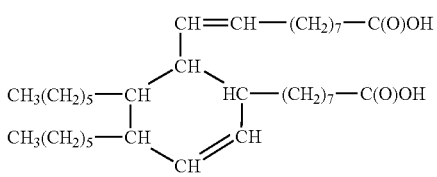

In a preferred embodiment the fiber is hair.
In a preferred embodiment the fiber is hair textile fiber.
In a preferred embodiment the fiber is hair fiber is paper.
In a preferred embodiment the effective concentration ranges from 0.1 to 15% by weight.
In a preferred embodiment e+f+g is an integer ranging from 15 to 30.

EXAMPLES RAW MATERIALS

Example 1 Dimer Acid

Dimer acid is an item of commerce and is available from a variety of sources including Cognis Chemical Cincinnati Ohio. It conforms to the following structure:

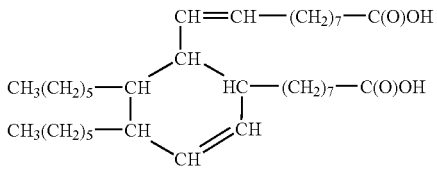

Example 2 Hydrogenated Dimer

Hydrogenated dimer acid is an item of commerce and is available from a variety of sources including Cognis Chemical Cincinnati Ohio. It conforms to the following structure:

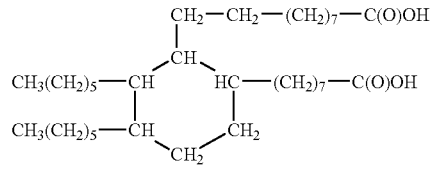

Polysorbates

Polysorbates are compounds of commerce, available from a variety of sources including Croda. They conform to the following structure:

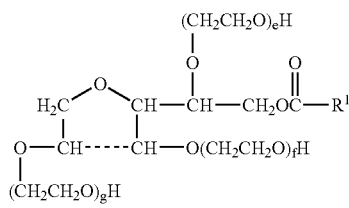

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;

| Example | e | f | g | e + f + g | $R^1$ |
|---|---|---|---|---|---|
| 3 | 3 | 3 | 3 | 9 | C11 |
| 4 | 7 | 7 | 7 | 21 | C15 |
| 5 | 7 | 7 | 7 | 21 | C17 |
| 6 | 7 | 7 | 7 | 21 | C21 |
| 7 | 10 | 10 | 10 | 30 | C11 |
| 8 | 8 | 8 | 8 | 24 | C11 |
| 9 | 17 | 16 | 17 | 50 | C11 |

(b) Di-hydroxyl Silicones

Di-hydroxyl silicones are compounds of commerce sold by Siltech LLC, Dacula, Ga. They conform to the following structure;

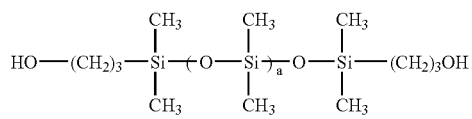

a is an integer ranging from 10 to 100;

| Example | a |
|---|---|
| 10 | 10 |
| 11 | 20 |
| 12 | 50 |
| 13 | 100 |

General Procedure
Preparation of Polyester.

To the specified number of grams of the specified polysorbate (Examples 3-9) and the specified number of grams of the specified di-hydroxyl silicone (Example 10-13). Is added 300 grams of dimer acid (Example 1 or 2). The reaction mass is heated to 180° C. The reaction proceeds as water is distilled off and the acid value becomes vanishingly small. The reaction is cooled and used as is in reaction sequence 2.
Dimer Acid Products
The 300 grams of dimer acid added are dimer acid Example 1.

| Example | Di-Hydroxyl Silicone | | Polysorbate | | Dimer:poly-sorbate:dihydroxyl silicone | Carboxy:hydroxyl |
|---|---|---|---|---|---|---|
| | Example | Grams | Example | Grams | | |
| 14 | 10 | 800 | 3 | 236 | 1:1:1 | 1:2 |
| 15 | 11 | 771 | 4 | 721 | 1:2:1 | 1:3 |
| 16 | 12 | 1880 | 5 | 437 | 1:1:1 | 1:2 |
| 17 | 13 | 3731 | 6 | 459 | 1:1:2 | 1:3 |
| 18 | 10 | 800 | 7 | 488 | 1:1:1 | 1:2 |
| 19 | 11 | 771 | 8 | 976 | 1:2:1 | 1:3 |
| 20 | 10 | 800 | 9 | 1668 | 1:2:1 | 1:3 |

Hydrogenated Dimer Acid Products

The 300 grams of dimer acid added are dimer acid Example 2.

| Example | Di-Hydroxy Silicone Example | Di-Hydroxy Silicone Grams | Polysorbate Example | Polysorbate Grams | Dimer:polysorbate:dihydroxyl silicone | Carboxy:hydroxyl |
|---|---|---|---|---|---|---|
| 21 | 10 | 800 | 3 | 236 | 1:1:1 | 1:2 |
| 22 | 11 | 771 | 4 | 721 | 1:2:1 | 1:3 |
| 23 | 12 | 1880 | 5 | 437 | 1:1:1 | 1:2 |
| 24 | 13 | 3731 | 6 | 459 | 1:1:1 | 1:3 |
| 25 | 10 | 800 | 7 | 488 | 1:1:1 | 1:2 |
| 26 | 11 | 771 | 8 | 976 | 1:2:1 | 1:3 |
| 27 | 10 | 3731 | 9 | 1668 | 1:2:1 | 1:3 |

Application Examples

Example 22 has the following composition: 16.5% hydrogenated dimer, 43% silicone and 40% polysorbate. This product is water dispersible, spontaneously forms an emulsion without added emulsifier and provides outstanding conditioning and softening to hair and skin.

For comparison; Example 23 has the following composition: 11.5% hydrogenated dimer 72% silicone 16.5% polysorbate. This product in stark contrast is water insoluble. It is a polar oil and provides cushion and skin feel when applied to hair and skin.

For comparison; Example 27 has the following composition: 11% hydrogenated dimer 29% silicone 60% polysorbate. This product in stark contrast is water soluble. It is a provides lubrication and moisturization when applied to hair and skin.

As can easily be seen the technology used to prepare the compounds of the present invention provide outstanding latitude to make roducts that have many desirable properties. This flexibility is highly desirable in a variety of applications.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A polymer consisting of a polyester made by the reaction of:

(a) a polysorbate conforming to the following structure $$\begin{array}{c} (CH_2CH_2O)_eH \\ | \\ O \\ | \\ H_2C\phantom{xx}O\phantom{xx}CH\phantom{x}CH\phantom{x}CH_2O\overset{O}{\overset{\|}{C}}{-}R^1 \\ | \phantom{xxxxxxxxxx} | \\ O{-}CH{-}{-}{-}{-}CH{-}O(CH_2CH_2O)_fH \\ | \\ (CH_2CH_2O)_gH \end{array}$$

e is an integer ranging from 0 to 30;
f is an integer ranging from 0 to 30;
g is an integer ranging from 0 to 30, with the proviso that e+f+g is an integer ranging from 9 to 50;
$R^1$ is alkyl having from 7 to 21 carbon atoms;
and (b) a di-hydroxyl silicone conforming to the following structure;

$$HO{-}(CH_2)_3{-}\underset{\underset{CH_3}{|}}{\overset{\overset{CH_3}{|}}{Si}}{-}(\!\!-\!\!O{-}\underset{\underset{CH_3}{|}}{\overset{\overset{CH_3}{|}}{Si}}\!\!-)_a O{-}\underset{\underset{CH_3}{|}}{\overset{\overset{CH_3}{|}}{Si}}{-}(CH_2)_3OH$$

a is an integer ranging from 10 to 100;
with dimer acid conforming to the following structure:

$$\begin{array}{c} \phantom{xxxxxxxxxxxx}CH{=}CH{-}(CH_2)_7{-}C(O)OH \\ \phantom{xxxxxxxxxxxxx}| \\ \phantom{xxxxxxxxxxxx}CH \\ CH_3(CH_2)_5{-}CH\phantom{xxx}HC{-}(CH_2)_7{-}C(O)OH \\ CH_3(CH_2)_5{-}CH\phantom{xxx}CH \\ \phantom{xxxxxxxxxxxx}CH \end{array}$$

or hydrogenated dimer acid conforming to the following structure:

$$\begin{array}{c} \phantom{xxxxxxxxxx}CH_2{-}CH_2{-}(CH_2)_7{-}C(O)OH \\ \phantom{xxxxxxxxxxx}| \\ \phantom{xxxxxxxxxx}CH \\ CH_3(CH_2)_5{-}CH\phantom{xxx}HC{-}(CH_2)_7{-}C(O)OH \\ CH_3(CH_2)_5{-}CH\phantom{xxx}CH_2 \\ \phantom{xxxxxxxxxx}CH_2 \end{array}$$

or mixtures thereof;
at a temperature of between 150 and 200° C., the mole ratio of said carboxyl groups in the dimer acid to hydroxyl group in the polysorbate range from 1:2 to 1:3.

2. A polymer of claim 1 wherein said dimer acid is hydrogenated dimer acid conforming to the following structure:

$$\begin{array}{c} \phantom{xxxxxxxxxx}CH_2{-}CH_2{-}(CH_2)_7{-}C(O)OH. \\ \phantom{xxxxxxxxxxx}| \\ \phantom{xxxxxxxxxx}CH \\ CH_3(CH_2)_5{-}CH\phantom{xxx}HC{-}(CH_2)_7{-}C(O)OH \\ CH_3(CH_2)_5{-}CH\phantom{xxx}CH_2 \\ \phantom{xxxxxxxxxx}CH_2 \end{array}$$

3. A polymer of claim 1 wherein said dimer acid is dimer acid conforming to the following structure:

$$\begin{array}{c} \phantom{xxxxxxxxxxxx}CH{=}CH{-}(CH_2)_7{-}C(O)OH. \\ \phantom{xxxxxxxxxxxxx}| \\ \phantom{xxxxxxxxxxxx}CH \\ CH_3(CH_2)_5{-}CH\phantom{xxx}HC{-}(CH_2)_7{-}C(O)OH \\ CH_3(CH_2)_5{-}CH\phantom{xxx}CH \\ \phantom{xxxxxxxxxxxx}CH \end{array}$$

4. A polymer of claim 1 wherein e+f+g is an integer ranging from 15 to 30.

5. A polymer of claim 2 wherein e+f+g is an integer ranging from 15 to 30.

6. A polymer of claim 3 wherein e+f+g is an integer ranging from 15 to 30.

7. A process for conditioning fiber which comprises contacting the fiber with an effective conditioning concentration of a polymer consisting of a polyester made by the reaction of:

(a) a polysorbate conforming to the following structure

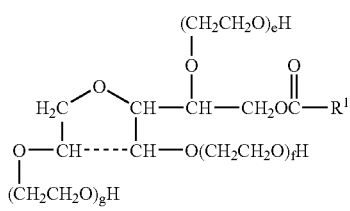

e is an integer ranging from 0 to 30;

f is an integer ranging from 0 to 30;

g is an integer ranging from 0 to 30, with the proviso that e+f+g is an integer ranging from 9 to 50;

$R^1$ is alkyl having from 7 to 21 carbon atoms;

and (b) a di-hydroxyl silicone conforming to the following structure;

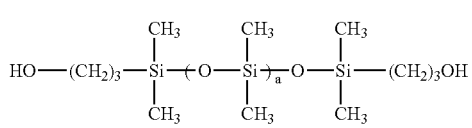

a is an integer ranging from 10 to 100;

with dimer acid conforming to the following structure:

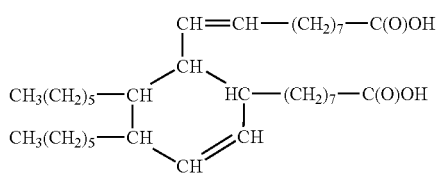

or hydrogenated dimer acid conforming to the following structure:

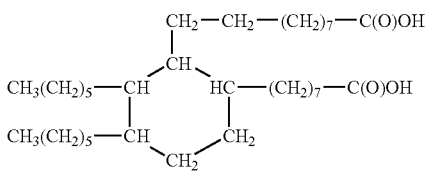

or mixtures thereof;

at a temperature of between 150 and 200° C., the mole ratio of said carboxyl groups in the dimer acid to hydroxyl group in the polysorbate range from 1:2 to 1:3.

8. A process of claim 7 wherein said dimer acid is hydrogenated dimer acid conforming to the following structure:

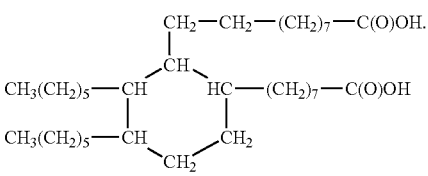

9. A process of claim 7 wherein said dimer acid is dimer acid conforming to the following structure:

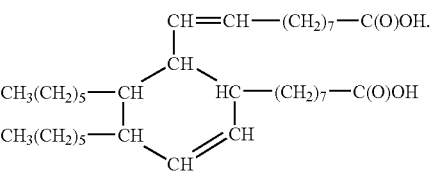

10. A process of claim 7 wherein said fiber is hair.

11. A process of claim 7 wherein said fiber is textile fiber.

12. A process of claim 7 wherein said fiber is paper.

13. A process of claim 8 wherein said fiber is hair.

14. A process of claim 8 wherein said fiber is textile fiber.

15. A process of claim 8 wherein said fiber is paper.

16. A process of claim 9 wherein said fiber is hair.

17. A process of claim 9 wherein said fiber is textile fiber.

18. A process of claim 9 wherein said fiber is paper.

19. A process of claim 7 wherein said effective conditioning concentration ranges from 0.1 to 15% by weight.

20. A process of claim 7 wherein e+f+g is an integer ranging from 15 to 30.

* * * * *